United States Patent
Niwa

Patent Number: 5,119,824
Date of Patent: Jun. 9, 1992

[54] HEARTBEAT SYNCHRONOUS WAVE DETECTING APPARATUS

[75] Inventor: Minoru Niwa, Nagoya, Japan

[73] Assignee: Colin Electronics Co., Ltd., Aichi, Japan

[21] Appl. No.: 531,769

[22] Filed: Jun. 1, 1990

[30] Foreign Application Priority Data

Jul. 27, 1989 [JP] Japan ................... 1-194542

[51] Int. Cl.⁵ ............................................. A61B 5/02
[52] U.S. Cl. ..................................... 128/687; 128/672; 128/680; 606/34
[58] Field of Search ............... 606/32, 34; 128/672, 128/677, 680, 681, 687, 689, 690, 696, 709, 710, 901, 419 R

[56] References Cited

U.S. PATENT DOCUMENTS

| | | | |
|---|---|---|---|
| 4,245,649 | 1/1981 | Andersen | 606/34 X |
| 4,331,157 | 5/1982 | Keller, Jr. et al. | 128/419 R |
| 4,928,700 | 5/1990 | Harada | 128/687 |
| 4,934,377 | 6/1990 | Bora et al. | 128/696 |

FOREIGN PATENT DOCUMENTS

0256155 2/1988 European Pat. Off. ............ 606/34

*Primary Examiner*—Lee S. Cohen
*Attorney, Agent, or Firm*—Oliff & Berridge

[57] ABSTRACT

An apparatus for detecting a heartbeat synchronous wave produced from a subject in synchronization with heartbeat of the subject, including a probe which is adapted to be set on a body portion of the subject, a sensor for detecting the heartbeat synchronous wave produced from the subject, the sensor being supported by the probe, a judging device for judging whether or not an electric knife is being used on the subject, and a device for, if the judging device judges that the electric knife is being used, ceasing from detecting the heartbeat synchronous wave, or discarding the heartbeat synchronous wave detected when the electric knife is being used. The judging device may be adapted to detect a high frequency electric current flowing from an electric knife to the probe via the body portion of the subject, and judge whether or not the electric knife is being used on the subject, based on the detected high frequency electric current.

20 Claims, 5 Drawing Sheets

HEARTBEAT SYNCHRONOUS WAVE DETECTING APPARATUS

BACKGROUND OF THE INVENTION

1. Field of the Invention

The present invention relates to an apparatus for detecting a heartbeat synchronous wave produced from a living body in synchronization with heartbeat of the subject, through a probe which is adapted to be set on a body portion of the subject. Such apparatus comprise a pulse wave detecting apparatus, a pulse oxymeter, and an electrocardiograph, for example.

2. Related Art Statement

The detector probe of the above apparatus is used on, for example, a patient who is undergoing a surgical operation, for monitoring dynamic function of the circulatory system of the patient during the operation. In a surgical operation an electric knife is often used for cutting a body portion of a patient for the purpose of hemostasis and sterilization of the cut portion. When a high frequency electric current is applied to the electric knife, however, a fraction of the electric current flows to the detector probe via the patient's body, and adversely affects the detection of a heartbeat synchronous wave through the probe. Since such apparatus are adapted to utilize a considerably weak electric signal representative of the detected heartbeat synchronous wave, a high frequency electric current flowing to the detector probe results in mixing noise into the electric signal detected through the probe. The electric signal containing noise is not appropriate to use for the determination of a blood pressure or a blood oxygen saturation of the patient. A doctor or a nurse may see the inaccurate information determined based on the inappropriate signal and consequently have incorrect views on the dynamic function of the circulatory system of the patient undergoing the surgery.

SUMMARY OF THE INVENTION

It is therefore an object of the present invention to provide a heartbeat synchronous wave detecting apparatus which is capable of judging whether or not an electric knife is being used on a subject whose heartbeat synchronous wave is detected thereby, and ensuring that a doctor or a nurse does not have incorrect views on dynamic function of the circulatory system of the subject based on an inappropriate heartbeat synchronous wave which is detected when the electric knife is being used on the patient.

The above object has been achieved by the present invention. According to a first aspect of the present invention, there is provided an apparatus for detecting a heartbeat synchronous wave produced from a subject in synchronization with heartbeat of the subject, comprising (a) a probe which is adapted to be set on a body portion of said subject, (b) sensor means for detecting the heartbeat synchronous wave produced from the subject, the sensor means being supported by the probe, (c) judging means for judging whether or not an electric knife is being used on the subject, and (d) means for, if the judging means judges that the electric knife is being used, ceasing from detecting the heartbeat synchronous wave, or discarding the heartbeat synchronous wave detected when the electric knife is being used.

The heartbeat synchronous wave detecting apparatus constructed as described above, has the means which, if the judging means judges that the electric knife is being used, ceases from detecting the heartbeat synchronous wave, or discards the heartbeat synchronous wave detected when the electric knife is being used. Thus, when the electric knife is being used, the present apparatus does not carry out the monitoring of dynamic function of the circulatory system of a subject based on a heartbeat synchronous wave. Therefore, the present apparatus ensures that a doctor or a nurse does not have incorrect views on the dynamic function of the circulatory system of a patient who is undergoing a surgical operation, from inaccurate information determined based on the inappropriate heartbeat synchronous wave detected when the electric knife is being used.

According to a second aspect of the present invention, there is provided an apparatus for detecting a heartbeat synchronous wave produced from a subject in synchronization with heartbeat of the subject, comprising (1) a probe which is adapted to be set on a body portion of the subject, (2) sensor means for detecting the heartbeat synchronous wave produced from the subject, the sensor means being supported by the probe, and (3) judging means for detecting a high frequency electric current flowing from an electric knife to the probe via the body portion, and judging whether or not the electric knife is being used on the subject, based on the detected high frequency electric current.

In the heartbeat synchronous wave detecting apparatus constructed as described above, the judging means detects a high frequency electric current flowing from an electric knife to the probe via the body portion, and judges whether or not the electric knife is being used on the subject, based on the detected high frequency electric current. Thus, the present apparatus is capable of detecting a high frequency electric current flowing from an electric knife, at a site spaced apart from a site where the electric knife is used, and therefore does not interfere with a surgeon who is operating the electric knife on the patient.

In a preferred embodiment according to the second aspect of the present invention, the apparatus further comprises means for ceasing, if the judging means judges that the electric knife is being used, from detecting the heartbeat synchronous wave.

In another embodiment according to the second aspect of the present invention, the apparatus further comprises means for discarding, if the judging means judges that the electric knife is being used, the heartbeat synchronous wave detected when the electric knife is being used.

In yet another embodiment of the apparatus of the present invention, the sensor means comprises at least one pressure sensing element, and a temperature sensing resistor means for sensing a temperature of the at least one pressure sensing element, the resistor means producing an electric signal representative of a body temperature of the body portion of the subject, the judging means comprising the temperature sensing resistor means, a magnitude of the electric signal being changeable upon flowing of the high frequency electric current to the at least one pressure sensing element via the body portion of the subject, the judging means detecting the high frequency electric current based on the changed magnitude of the electric signal.

In a further embodiment of the apparatus of the present invention, the probe comprises a housing including a first and a second portion each formed of an electrically conductive material, and an electrically insulating member inserted between the first and second portions, the first portion being grounded and spaced from the body portion of the subject while the second portion contacting the body portion, the judging means comprising the housing, and a resistor member connected at opposite ends thereof to the first and second portions of the housing, respectively, a voltage between the opposite ends of the resistor member being changeable upon flowing of the high frequency electric current to the second portion of the housing via the body portion of the subject, the judging means detecting the high frequency electric current based on the changed voltage between the opposite ends of the resistor member.

In a still further embodiment of the apparatus of the present invention, the judging means judges that the electric knife is being used, if the judging means detects a high frequency electric current greater than a first reference value. In this case, the judging means may be adapted to judge that the electric knife is being used, if the judging means continues to detect the high frequency electric current for more than a first reference time.

In an advantageous form of the above embodiment, the apparatus may further comprise, when the judging means is a first judging means, a second judging means for judging whether or not the electric knife is not being used any longer after use thereof. In this case the second judging means may be adapted to judge that the electric knife is not being used any longer, if the second judging means detects that the high frequency electric current greater than the first reference value has become smaller than a second reference value smaller than the first reference value. In addition, the second judging means may be adapted to judge that the electric knife is not being used any longer, if the second judging means continues to detect the high frequency electric current smaller than the second reference value for more than a second reference time. The second judging means may further judge whether or not the subject has become free from the high frequency electric current and highly stable after the use of the electric knife.

According to a feature of the present invention, the apparatus further comprises means for storing the heartbeat synchronous wave detected by the sensor means when the electric knife is not being used, and means for utilizing, if the judging means judges that the electric knife is being used, the heartbeat synchronous wave detected and stored before the use of the electric knife.

According to another feature of the apparatus of the present invention, the sensor means comprises a pulse wave sensor means for detecting a pulse wave produced from an arterial vessel in the body portion of the subject in synchronization with heartbeat of the subject.

BRIEF DESCRIPTION OF THE DRAWINGS

The above and optional objects, features and advantages of the present invention will be better understood by reading the following detailed description of the presently preferred embodiment of the invention when considered in conjunction with the accompanying drawings, in which.

DETAILED DESCRIPTION OF THE PREFERRED EMBODIMENT

Figure 1:
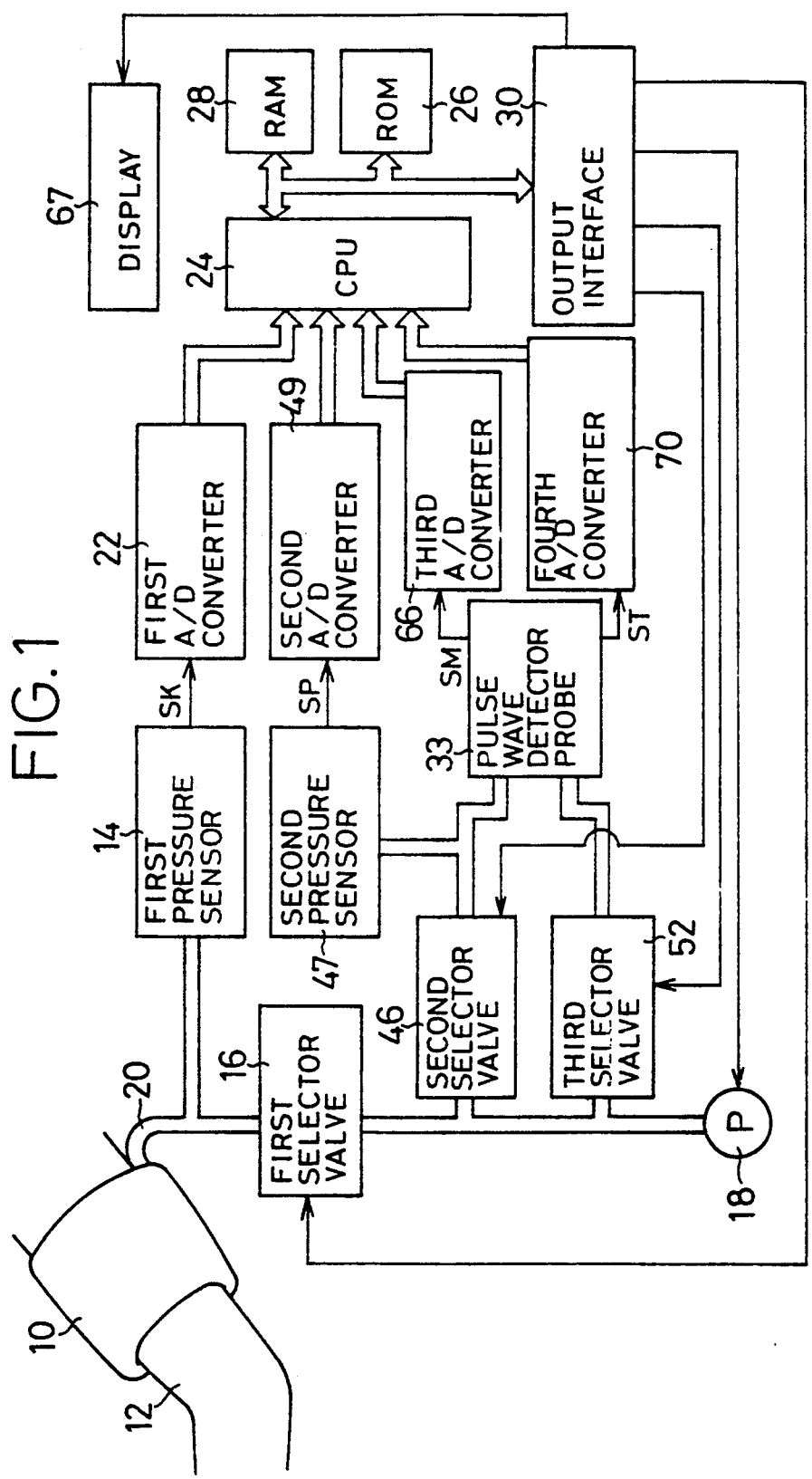
FIG. 1 is a diagrammatic view of a blood pressure monitoring apparatus having a pulse wave detecting device, in which the present invention is embodied.

Referring first to FIG. 1 there is shown a blood pressure monitoring apparatus for monitoring blood pressure of a subject by detecting a pulse wave produced from an arterial vessel of the subject in synchronization with heartbeat of the subject. In the figure reference numeral 10 designates an inflatable cuff consisting essentially of a rubber bag. The cuff 10 is wound around an upper arm 12 of the subject to press the upper arm 12. The cuff 10 is connected via a piping 20 to a first pressure sensor 14, a first selector valve 16, and an electric pump 18. The pump supplies a pressurized fluid, for example a pressurized air, to the cuff 10 so as to inflate the cuff 10 and thereby increase a fluid pressure in the cuff 10 (hereinafter, referred to as the "cuff pressure"). The first pressure sensor 14 detects timewise variation in the cuff pressure, and generates a cuff pressure signal SK representative of the detected variation in the cuff pressure, to a central processing unit (CPU) via a first analog to digital (A/D) converter 22. The first selector valve 16 is selectively placed in a first position ("INFLATION"), a second position ("SLOW DEFLATION") and a third position ("RAPID DEFLATION") thereof. In the INFLATION position the first selector valve 16 permits the pressurized fluid from the pump 18 to be supplied therethrough to the cuff 10, so that the cuff pressure is increased. In the SLOW DEFLATION position the valve 16 permits the fluid in the cuff 10 to be slowly deflated therethrough, so that the cuff pressure is slowly decreased. In the RAPID DEFLATION position the valve 16 permits the fluid in the cuff 10 to be rapidly deflated therethrough, so that the cuff pressure is rapidly decreased.

The CPU 24 is coupled via data bus to a read only memory (ROM) 26, a random access memory (RAM) 28, and an output interface 30. The CPU 24 processes the received signal SK according to programs prestored in the ROM 26 by utilizing the temporary storage function of the RAM 28. The CPU 24 activates and deactivates the electric pump 18 via a drive circuit (not shown) and changes the positions of the first selector valve 16 via another drive circuit (not shown), so as to increase and decrease the cuff pressure. When the cuff pressure is slowly decreased, the CPU 24 operates for determining a systolic (maximum) blood pressure and a diastolic (minimum) blood pressure of the subject based on variation in amplitude of the alternating component of the signal SK representative of the cuff pressure.

Figure 2:
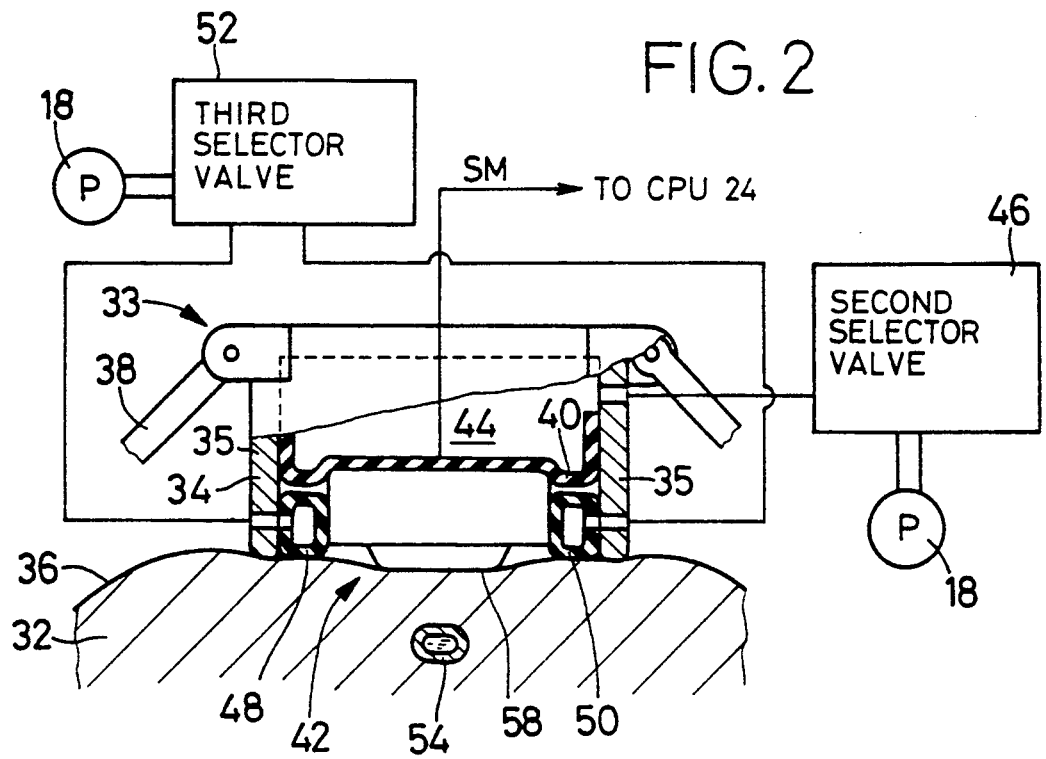
FIG. 2 is a view illustrating a pulse wave detector probe of the apparatus of FIG. 1 (partially in cross section) set on a wrist of a patient.
Figure 3:
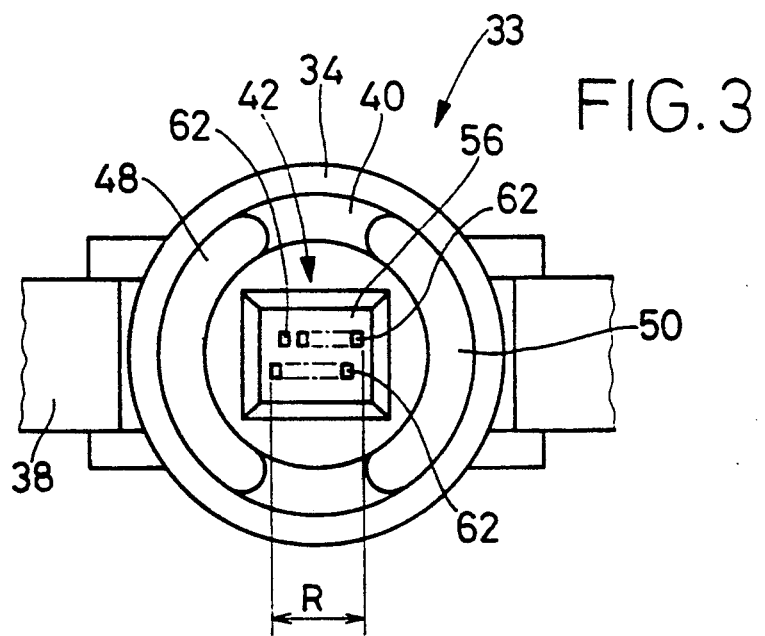
FIG. 3 is a view of the detector probe of FIG. 2 as seen from the side of the wrist.

Referring next to FIGS. 2 and 3 there is shown a pulse wave detector probe 33 through which a pulse wave is detected from a radial artery 54 in a wrist 32 of the subject. The detector probe 33 is detachably set on the wrist 32 with the help of a wrist band 38. The detector probe 33 includes a cylindrical metallic housing 34 with a bottom and an opening at opposite axial ends thereof. With the detector probe 33 set on the wrist 32, the open end of the housing 34 contacts a surface (skin) 36 of the wrist 32. The detector probe 33 further includes a diaphragm 40 which is secured to an inner wall surface of the housing 34 and cooperates with the housing 34 to define a pressure chamber 44 inside the detector probe 33. A pulse wave sensor 42 is secured to an outer, lower surface of the diaphragm 40 such that the sensor 42 is movable with the diaphragm 40 relative to the housing 34 and is advanceable toward the body surface 36 through the open end of the housing 34. The pressure chamber 44 is supplied with a pressurized fluid from the electric pump 18 via a second selector valve 46, so that the pulse wave sensor 42 is pressed against the body surface 36 with a pressing force which is variable depending on a fluid pressure P in the pressure chamber 44. The second selector valve 46 is selectively placed in a first position ("SLOW PRESSURE INCREASE"), a second position ("PRESSURE HOLD"), and a third position ("PRESSURE DECREASE") thereof. In the SLOW PRESSURE INCREASE position the second selector valve 46 permits the fluid from the pump 18 to be slowly supplied therethrough to the pressure chamber 44, so that the fluid pressure P in the pressure chamber 44 is slowly increased. In the PRESSURE HOLD position the valve 46 serves for maintaining the fluid pressure P. In the PRESSURE DECREASE position the valve 46 permits the fluid from the pressure chamber 44 to be discharged therethrough, so that the fluid pressure P is decreased. Between the second selector valve 46 and the pressure chamber 44 there is disposed a second pressure sensor 47 (FIG. 1) for detecting the fluid pressure P in the pressure chamber 44 and generates a pressure signal SP indicative of the detected fluid pressure P, to the CPU 24 via a second A/D converter 49.

A pair of generally semicircular rubber bags 48, 50 are disposed between the pulse wave sensor 42 and the inner wall surface of the housing 34, in the neighborhood of the open end of the housing 34, such that the pair of rubber bags 48, 50 are secured to a pair of side walls 35, 35 of the housing 34, respectively, to which the wrist band 38 are connected. The first and second rubber bags 48, 50 are sandwiched between the sensor 42 and the corresponding side walls 35, 35. The rubber bags 48, 50 each are supplied with a pressurized fluid from the electric pump via a third selector valve 52. The selector valve 52 is selectively placed in a first position ("INFLATION/DEFLATION"), a second position ("DEFLATION/INFLATION"), a third position ("DEFLATION INHIBIT"), and a fourth position ("DEFLATION/DEFLATION") position. In the INFLATION/DEFLATION position the third selector valve 52 permits the pressurized fluid from the pump 18 to be supplied therethrough to the first rubber bag 48 and concurrently permits the fluid from the second rubber bag 50 to be discharged therethrough. In the DEFLATION/INFLATION position the valve 52 permits the fluid from the first rubber bag 48 to be discharged therethrough and concurrently the pressurized fluid from the pump 18 to be supplied therethrough to the second rubber bag 50. In the DEFLATION INHIBIT position the valve 52 inhibits the deflation of each of the first and second rubber bags 48, 50. In the DEFLATION/DEFLATION position the valve 52 permits the fluid from each of the first and second rubber bags 48, 50 to be discharged therethrough. Thus, the pulse wave sensor 42 is displaceable in a direction generally perpendicular to the radial artery 54, by changing the positions of the third selector valve 52 and thereby selectively supplying the pressurized fluid from the electric pump 18 to the first or second rubber bag 48, 50.

Figure 4:
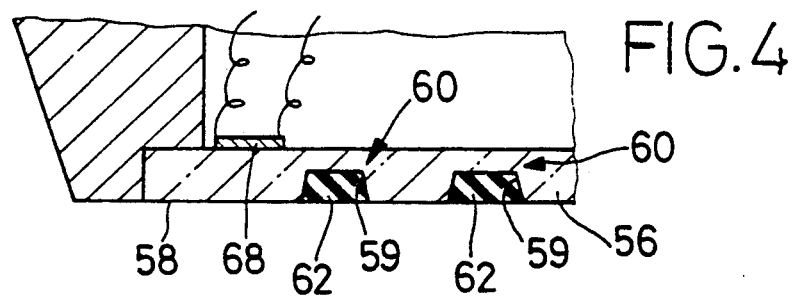
FIG. 4 is a cross sectional view of a portion of a pulse wave sensor of the detector probe of FIG. 2.

As shown in FIGS. 3 and 4 the pulse wave sensor 42 includes a semiconductor substrate 56 such as a monocrystalline silicon. The substrate 56 is pressed at a pressing surface 58 thereof against the body surface 36 of the wrist 32. A number of recesses 59 are formed in the pressing surface 58 such that two rows of recesses 59 are alternately provided. A pressure sensing diode 60 is formed in a thin portion (of the substrate 56) defining the bottom of each of the recesses 59. This thin portion has an extremely small thickness, for example 15 m$\mu$, although the thin portion is illustrated in FIG. 4 as if it had a comparatively large thickness. An elastic rubber member 62 is accommodated in each of the recesses 59. With the detector probe 33 set on the body surface 36 of the wrist 32, the two rows of pressure sensing diodes 60 cross over the radial artery 54 in the direction generally perpendicular thereto. When the pulse wave sensor 42 is pressed against the radial artery 54 via the body surface 36, pressure oscillation or pressure pulse wave produced from the radial artery 54 in synchronization with heartbeat of the subject, is transmitted to each of the pressure sensing diodes 60 via the corresponding rubber members 62, whereby pressure variation corresponding to the pulse wave is produced at the P/N (positive and negative) interface of each diode 60. Consequently, an electric signal, SM, representative of the transmitted pulse wave is generated between a common terminal (not shown) and each of individual terminals (not shown) of the diodes 60. The pulse wave signal SM is supplied to the CPU 24 via a third A/D converter 66. In the present embodiment, the pulse wave produced from the radial artery 54 serves as a heartbeat synchronous wave. The CPU 24 commands a display 67 (FIG. 1) to indicate a waveform corresponding to the pulse wave signal SM. In addition, the CPU 24 operates for determining a blood pressure of the subject based on variation in magnitude of the pulse wave signal SM, and commands the display 67 to indicate the determined blood pressure value.

A temperature sensing resistor device 68, which is known in the art, is provided on the semiconductor substrate 56. The resistor device 68 serves for temperature compensation of the pressure sensing diodes 60. The resistor device 68 detects a body temperature of a portion of the wrist 32 against which the pulse wave sensor 42 (the semiconductor substrate 56) is pressed, and generates a body temperature signal ST representative of the detected body temperature, to the CPU 24 via a fourth A/D converter 70. The CPU 24 judges whether or not an electric knife 72 (FIG. 5, described below) is being used, based on timewise variation in magnitude of the signal ST. When the electric knife 72 is being used, the CPU 24 operates for ceasing from detecting the pulse wave and from monitoring the blood pressure. Meanwhile, when the use of the electric knife 72 is terminated, the CPU 24 operates for resuming the detection of the pulse wave, and the monitoring of the blood pressure based on the pulse wave.

Figure 5:
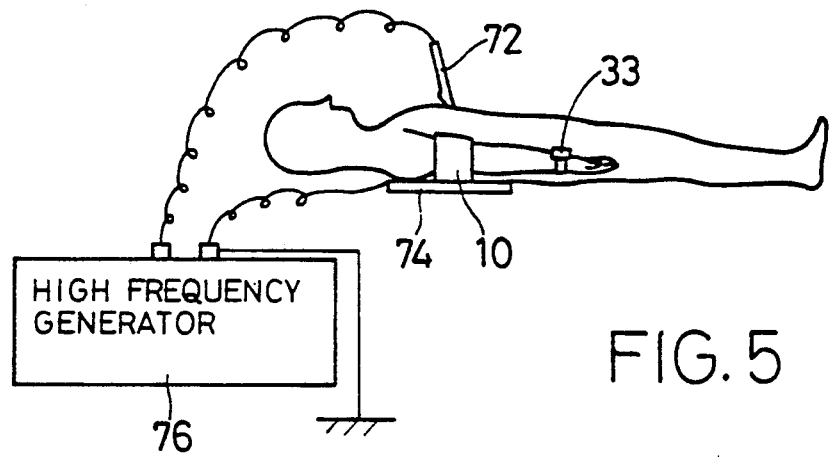
FIG. 5 is a view illustrating an electric knife being used for cutting a body portion of the patient, the detector probe of FIG. 2 being set on the wrist of the patient.

The blood pressure monitoring apparatus constructed as described is used for, for example, monitoring dynamic function of the circulatory system of a patient which is undergoing a surgical operation. As shown in FIG. 5 an electric knife 72 may be used on the patient in the operation. In this event an electrode in the form of a large plate 74 is placed under the back of the patient. The electric knife 72 and the electrode plate 74 are connected to respective terminals of a high frequency generator 76. The terminal to which the electrode plate 74 is connected, is grounded. When the electric knife 72 is used to cut a body portion of the patient, a high frequency electric current is passed from the electric knife 72 to the electrode plate 74 through the patient's body, so that the tip of the electric knife 72 produces heat for hemostasis and sterilization of the cut portion. On the other hand, a fraction of the high frequency current flows from the electric knife 72 to the body portion under the detector probe 33 via the patient's arm 12 and the semiconductor substrate 56 of the pulse wave sensor 42, thereby causing a variation in the voltage between the output terminals of the temperature sensing resistor 68 from which the body temperature signal ST is produced. Stated differently, when the electric knife 72 is being used on the patient, a corresponding variation occurs to the magnitude of the signal ST. Thus, it is possible to detect the use of the electric knife 72 based on the signal ST. In addition, the high frequency current flowing to the pulse wave sensor 42 results in mixing noise into the pulse wave signal SM produced by the sensor 42, thereby deteriorating the accuracy of detection of the pulse wave.

Figure 6:
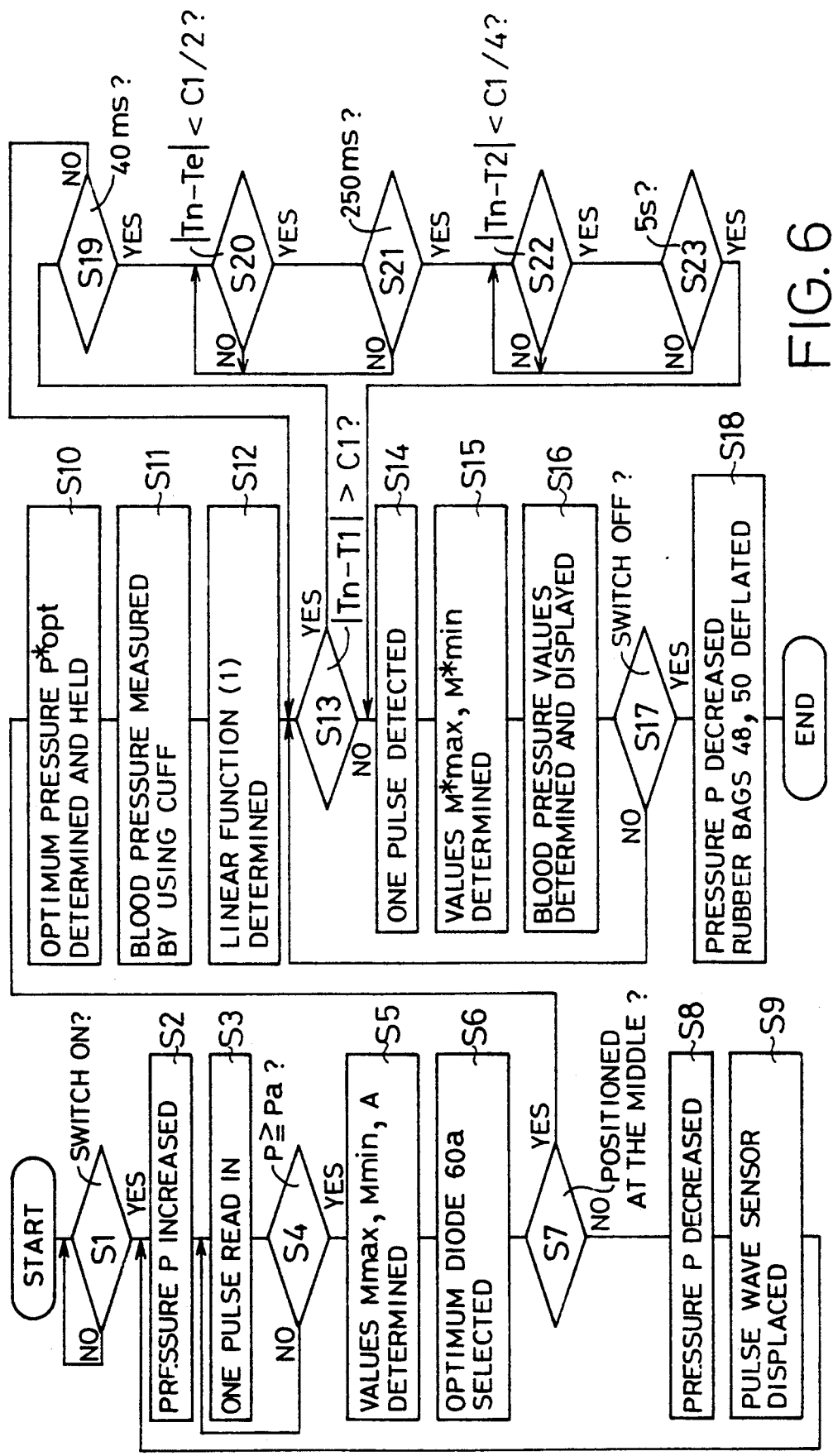
FIG. 6 is a flow chart according to which the monitoring apparatus of FIG. 1 is operated to monitor blood pressure of the patient.

Hereinafter there will be described the operation of the above-described blood pressure monitoring apparatus by reference to the flow chart of FIG. 6.

First the inflatable cuff 10 and the pulse wave detector probe 33 are set on the upper arm 12 and the wrist 32 of the subject, respectively. Upon application of electric power thereto, an initialization step (not shown) is carried out on the monitor apparatus. Subsequently the control of the CPU 24 proceeds with Step S1 in which it is judged whether or not a START/STOP switch (not shown) has been operated to its START or ON position. If the judgement in Step S1 is negative (NO), the control of the CPU 24 remains in Step S1. Meanwhile, if the judgement in Step S1 is turned affirmative (YES), the control proceeds with Step S2 in which the electric pump 18 is activated and the second selector valve 46 is placed in its SLOW PRESSURE INCREASE position, so that a slow increase in the fluid pressure P is initiated in the pressure chamber 44 of the detector probe 33 and that the pulse wave sensor 42 is pressed against the body surface 36 as the fluid pressure P is slowly increased. Step S2 is followed by Step S3 in which the CPU 24 reads in a pulse wave signal SM corresponding to a dilation and a contraction of the heart of the subject, that is, one pulse SM(1), together with a pressure signal SP representative of the slow pressure increase in the fluid pressure P. Step S3 is followed by Step S4.

In step S4 it is judged whether or not the fluid pressure P has exceeded a reference value Pa. If the judgement in Step S4 is negative, the control of the CPU 24 repeats Steps S3 and S4 and each time reads in one pulse SM(1) together with the corresponding signal SP. Meanwhile, if the judgement in Step S4 is turned affirmative, the control goes to step S5 in which a maximum magnitude Mmax (mV) and a minimum magnitude Mmin (mV) of one pulse SM(1) read in in Step S3 are determined with respect to the pulse wave signal SM from each of the pressure sensing diodes 60, and an amplitude A of each pulse wave signal SM is determined by calculating a difference between the maximum and minimum magnitudes Mmax, Mmin. Step S5 is followed by Step S6 in which the largest amplitude A* is selected from the amplitudes A determined with respect to the pulse wave signals SM from the diodes 60, and the diode 60 which produces the pulse wave signal SM having the largest amplitude A* is determined as an optimum diode 60a.

Step S6 is followed by Step S7 in which it is judged whether or not the selected optimum diode 60a is positioned in a middle portion of a detection range R (FIG. 3) corresponding to a length of arrangement of the two rows of diodes 60. If the judgement in Step S7 is negative, the control of the CPU 24 proceeds with step S8 in which the second selector valve 46 is switched from the SLOW PRESSURE INCREASE position to the PRESSURE DECREASE position, so as to decrease the fluid pressure P in the pressure chamber 44, thereby permitting the pulse wave sensor 42 to be displaced in the direction perpendicular to the direction of extension of the radial artery 54. Step S8 is followed by step S9 in which the pulse wave sensor 42 is displaced in the above-indicated perpendicular direction by placing the third selector valve 52 in an appropriate position and thereby pressurizing the first or second rubber bag 48, 50. Thus, the middle portion of the detection range R is aligned with the radial artery 54. Following Step S9 the control of the CPU 24 goes back to Step S2.

If in Step S7 it is judged that the selected optimum diode 60a has its position in the middle portion of the detection range R, that is, if the judgement in Step S7 is affirmative, the control of the CPU 24 proceeds with Step S10 in which a fluid pressure in the pressure chamber 44 when the optimum diode 60a produces a pulse wave SM having a maximum amplitude A*max, is determined as an optimum pressure P*opt, that is, the most appropriate pressure for pressing the pulse wave sensor 42 against the radial artery 54 via the body surface 36. In addition, the fluid pressure P is adjusted to the determined optimum pressure P*opt. Subsequently the second selector valve 46 is placed in its PRESSURE HOLD position so as to maintain the optimum pressure P*opt and thereby press the pulse wave sensor 42 against the body surface 36 with the optimum pressure P*opt.

Step S10 is followed by step S11 in which a blood pressure of the subject is measured by the "oscillometric" method. Specifically, the first selector valve 16 is placed in its INFLATION position so as to increase the cuff pressure to a reference value (e.g., 180 mmHg) which is speculated to be higher than a systolic (maximum) blood pressure of the subject. Subsequently the electric pump 18 is deactivated and the first selector valve 16 is switched to its SLOW DEFLATION position, so as to slowly decrease the cuff pressure. In this slow cuff pressure decrease process the CPU 24 reads in a cuff pressure signal SK representative of the cuff pressure, and operates for determining a systolic blood pressure H (mmHg) and a diastolic blood pressure L (mmHg) based on variation in amplitude of the alternating component of the signal SK. Following completion of the blood pressure measurement, the first selector valve 16 is switched to its RAPID DEFLATION position so as to rapidly deflate the cuff 10.

Subsequently the control of the CPU 24 goes to Step S12 in which is determined the following linear function (I) according to which an actual blood pressure $P_B$ (e.g., systolic and diastolic blood pressure values SYS, DIA) of the subject is determined based on a magnitude M (e.g., maximum and minimum magnitudes M*max, M*min) of each pulse SM(1) of the pulse wave signal SM supplied from the optimum diode 60a pressed with the optimum pressure P*opt. The linear function (I) defines a relationship between blood pressure $P_B$ and pulse wave magnitude M:

$$P_B = a.M + b \quad (I)$$

$$H = a.M^*max + b \quad (a)$$

$$L = a.M^*min + b \quad (b)$$

The linear function (I), or constants a and b thereof are determined by solving the simultaneous linear equations (a) and (b) in which are used the values H, L determined in Step S11 and the values M*max, M*min determined in Step S5.

Step S12 is followed by step S13 in which it is judged whether or not the absolute value of a difference between a magnitude Tn of a last body temperature signal STn and a magnitude T1 of a body temperature signal ST1 which had been read in 150 ms before the last signal STn is read in, exceeds a predetermined constant value C1. This constant value C1 corresponds to a reference magnitude of the high frequency current flowing from the electric knife 72 to the detector probe 33 on one hand, and on the other hand corresponds to a certain variation in magnitude of the pulse wave signal SM. This certain variation corresponds to, for example, an about 15 mmHg blood pressure increase or decrease. In other words, when a high frequency current corresponding to a more than about 15 mmHg blood pressure increase or decrease, flows from the electric knife 72 to the pulse wave sensor 42 (or the body portion thereunder), the magnitude of each of the body temperature signal ST and the pulse wave signal SM is correspondingly changed, and the judgement in Step S13 is found affirmative. Each of the values Tn and T1 is preferably obtained by averaging the magnitudes of four consecutive signals read in at 5 ms intervals. If the judgement in Step S13 is negative, the CPU 24 judges that the electric knife 72 is not being used, and the control of the CPU 24 proceeds with Step S14.

In Step S14 the CPU 24 reads in a one pulse SM(1) through the optimum diode 60a. Step S14 is followed by Step S15 in which are determined maximum and minimum magnitudes M*max and M*min of the one pulse SM(1) read in in Step S14. Subsequently in Step S16 systolic and diastolic blood pressure values SYS, DIA are determined based on these values M*max, M*min according to the linear function (I), and the determined values SYS, DIA are indicated on the display 67. The display 67 is adapted to indicate the waveform of the one pulse SM(1) read in in Step S14, together with the values SYS, DIA. Step S16 is followed by step S17 in which it is judged whether or not the START/STOP switch has been operated to its STOP (OFF) position. If the judgement in Step S17 is negative, the control of the CPU 24 repeats Steps S13–S17 and thus monitors the blood pressure of the subject. Meanwhile, if the judgement in Step S17 is turned affirmative, the control proceeds with Step S18 in which the pressure chamber 44 and the first and second rubber bags 48, 50 are deflated and thus the blood pressure monitoring is terminated.

Meanwhile, if the judgement in Step S13 is affirmative, the control of the CPU 24 goes to Step S19 in which it is judged whether or not the affirmative judgement in Step S13 has continued for more than a reference time, for example 40 ms. If the judgement in Step S19 is affirmative, the CPU 24 judges that the electric knife 72 is being used on the patient, and the control of the CPU 24 goes to Step S20. Thus, in the present embodiment the temperature sensing resistor 68, Step S13, Step S19 and others cooperate with each other to serve as judging means for detecting a high frequency electric current flowing from the electric knife 72 to the probe 33 via the body portions 12, 32, and judging whether or not the electric knife 72 is being used on the subject based on the detected high frequency electric current.

Step S20 is followed by Step S21 in which it is judged whether or not the absolute value of a difference between a magnitude Tn of a last body temperature signal STn and a magnitude Te of a body temperature signal STe which had been read in in Step S13 when the use of the electric knife 72 is detected, is smaller than a predetermined constant C2 ($=(C1)/2$, a half of the value C1). At an early stage the judgement in Step S20 is negative, and the control of the CPU 24 repeats Step S21. Meanwhile, if the judgement in Step S20 is turned affirmative, the control goes to Step S21 in which it is judged whether or not the affirmative judgement in Step S21 have continued for more than a reference time, for example 250 ms. If the judgement in Step S21 is affirmative, that is, if it is judged that the magnitude of the body temperature signal ST has almost been recovered to a value before the use of the electric knife 72, Step S21 is followed by Step S22.

In Step S22 it is judged whether or not the absolute value of a difference between a magnitude Tn of a last body temperature signal STn and a magnitude T2 of a body temperature signal ST2 which had been read in 150 ms before the signal STn, is smaller than a predetermined constant C3 ($=(C1)/4$, a quarter of the value Cl). If the judgement in Step S22 is negative, the control of the CPU 24 remains in Step S22. Meanwhile, if judgement is turned affirmative, Step S22 is followed by Step S23 in which it is judged whether or not the affirmative judgement in Step S22 have continued for more than a reference time, for example 5 seconds. At an early stage the judgement in Step S23 is negative, and the control of the CPU 24 repeats Step S23. Meanwhile, if the judgement in Step S23 is turned affirmative, the CPU 24 concludes that the body temperature signal ST has become sufficiently stable at a magnitude almost equal to the magnitude before the detection of use of the electric knife 72 because the patient's body has become free from the high frequency current, and therefore that the use of the electric knife 72 has been terminated. Subsequently the control of the CPU 24 goes back to Step S14 and the following steps, thus resuming detection of the pulse wave and monitoring of the blood pressure based on the pulse wave. In the present embodiment, while the control of the CPU 24 remains in Steps S19–S23, the detection of pulse wave and the monitoring of blood pressure monitoring are temporarily ceased. Hence Steps S19–S23 serves as means for ceasing, if the judging means judges that the electric knife 72 is being used on the patient, from detecting the pulse wave as a heartbeat synchronous wave. While the pulse wave detection and the blood pressure monitoring are not carried out due to the use of the electric knife 72, the display 67 indicates the pulse wave waveform and the blood pressure values (e.g., values SYS and DIA) detected and determined immediately before the detection of use of the electric knife 72.

As is understood from the foregoing description, when the electric knife 72 is being used on a patient, the high frequency electric current which is passed from the electric knife 72 to the electrode plate 74 through the patient's body, partially flows through the patient's arm and wrist to the pulse wave sensor 42 of the detector probe 33. Consequently, the voltage between the output terminals of the temperature sensing resistor device 68 is changed, and the magnitude of the body temperature signal ST generated by the resistor device 68 is changed. Thus, the present blood pressure monitoring apparatus is capable of detecting that the electric knife 72 is being used on the patient. When detecting that the electric knife 72 is being used, the present monitor apparatus ceases from detecting the pulse wave from the patient and from monitoring the blood pressure of the patient. Thus, during use of an electric knife on a patient the present apparatus does not monitor dynamic function of the circulatory system of the patient based on blood pressure readings. In other words, the present apparatus is capable of avoiding a doctor or a nurse from having incorrect views on the dynamic function of the circulatory system of the patient based on the inappropriate pulse wave or inaccurate blood pressure readings obtained during use of the electric knife 72.

In the present embodiment, the temperature sensing resistor device 68 serving for the temperature compensation of the pressure sensing diodes 60, is simultaneously utilized for judging whether or not the electric knife 72 is being used on a patient. Thus, the cost of manufacture of the present monitor apparatus is not so increased.

Furthermore, the present monitor apparatus is adapted not to judge that the use of the electric knife 72 has been ended, until the magnitude of the body temperature signal ST has become sufficiently stable after the magnitude has almost been recovered to the value before the use of the electric knife 72. In other words, the present apparatus does not resume the detection of pulse wave or the monitoring of blood pressure in the event that the magnitude of the signal ST is recovered only in an instantaneous period of time. However, Steps S22 and S23 may be omitted from the flow chart of FIG. 6. In this case the CPU 24 is adapted to judge that the use of the electric knife 72 has been ended if the judgement in Step S21 is affirmative.

While the present invention has been described in its preferred embodiment with particularities, it is to be understood that the present invention may be embodied with various modifications.

Figure 7:
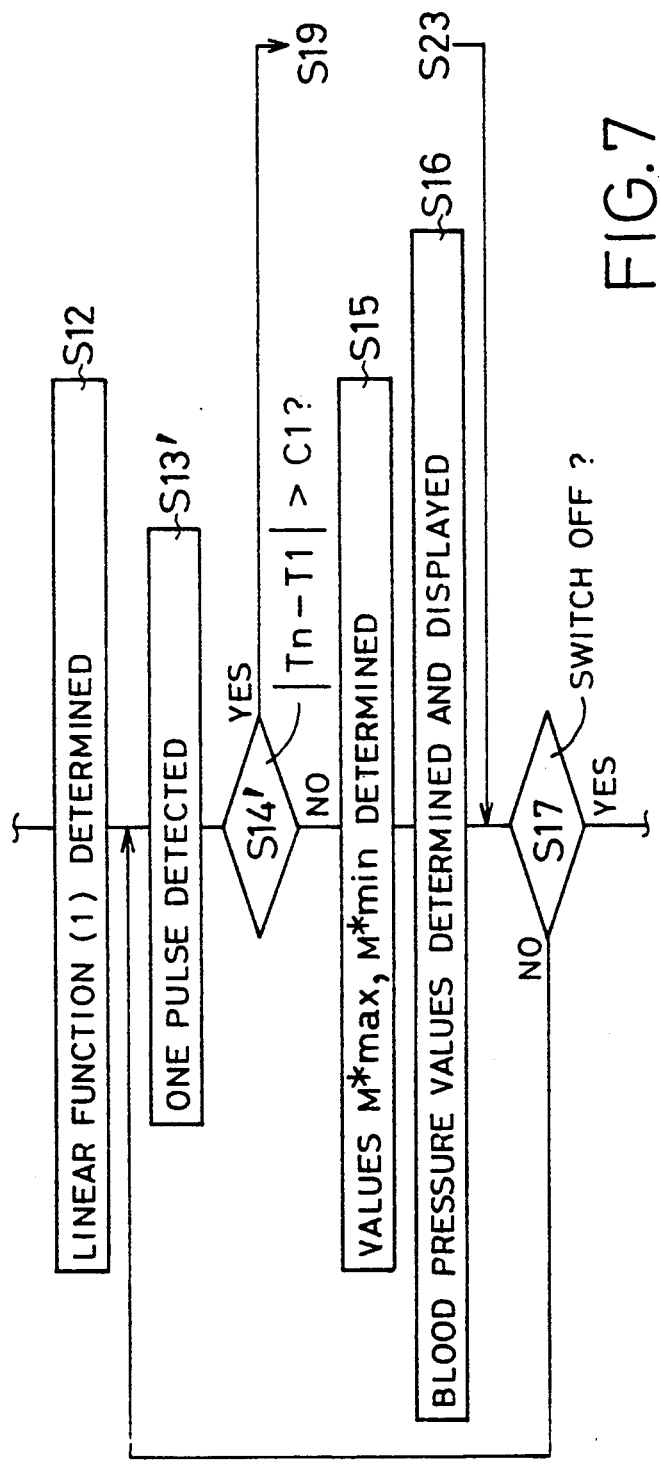
FIG. 7 is a portion of a flow chart according to which another embodiment of the present invention is operated.

For example, while in the illustrated embodiment the detection of pulse wave is ceased during use of the electric knife 72, it is possible to detect the pulse wave even during use of the electric knife 72 but cease from monitoring the blood pressure based on the detected pulse wave. In this case a pertinent portion of the flow chart of FIG. 6 is replaced with the flow chart of FIG. 7.

In the illustrated embodiment, the algorithm associated with the detection of use of the electric knife 72 is carried out after the pulse wave sensor 42 is automatically positioned in the middle portion thereof directly above the radial artery 54 and the optimum pressing force P*opt with which to press the sensor 42 against the body surface 36 is automatically determined. However, in the event that the influence of the displacement motion of the sensor 42 to the magnitude of the body temperature signal ST, or the influence of the pressing action of the sensor 42 to the magnitude of the signal ST, can be accurately distinguished from the influence of the use of the electric knife 72 to the magnitude of the signal ST, it is possible to carry out the above algorithm before or after Step S3, so as to detect an accurate pulse wave free from the influence of the use of the electric knife 72 (or from the high frequency electric current flowing therefrom). In this event, the positioning of the pulse wave sensor 42 or the determination of the optimum pressing force P*opt is carried out in a more reliable manner, and in Step S12 is determined a more accurate relationship between blood pressure and pulse wave signal magnitude (that is, the linear function (I)). When detecting that the electric knife 72 is being used, the instant modified apparatus ceases from increasing the fluid pressure P in the pressure chamber 44.

The determination of the blood pressure and pulse wave relationship in Step S12 may be carried out based on a pulse wave detected after the optimum pressure P*opt has been determined in Step S10. In this case, too, the algorithm for the detection of use of the electric knife 72 may be executed before or after detection of the pulse wave. In this case, the determination of the relationship in Step S12 is made based on a more accurate pulse wave signal SM which is free from the influence resulting from use of the electric knife 72.

Figure 8:
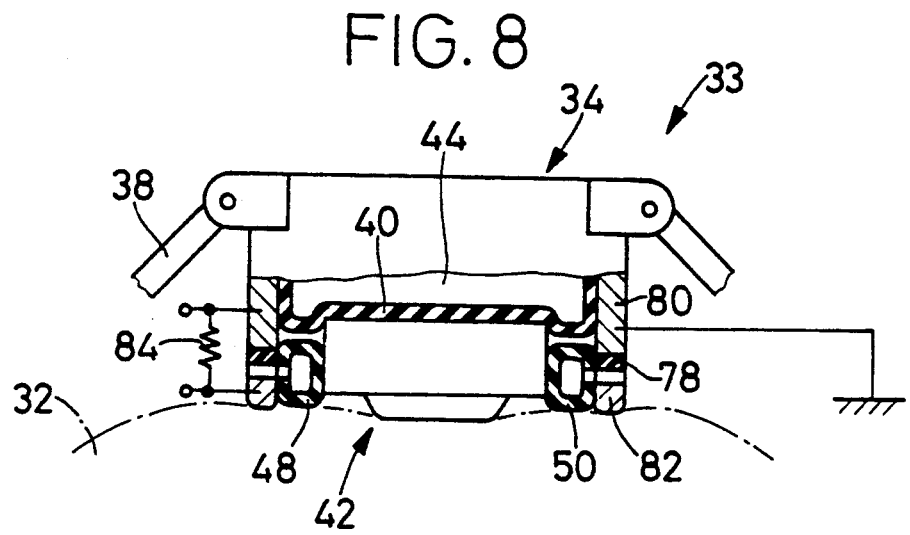
FIG. 8 is a view corresponding to FIG. 2, showing another detector probe employed in the present invention.

While in the illustrate embodiment the temperature sensing resistor device 68 for the temperature compensation of the pressure sensing diodes 60, is diverted as a sensing means for detecting a high frequency electric current, it is possible to replace the resistor device 68 with a sensing means as shown in FIG. 8. This sensing device is provided integral with a housing 34 of a pulse wave detector probe 33. The sensing device includes a first and a second portion 80, 82 of the housing 34. The first and second housing portions 80, 82 are formed of metal, and electrically insulated by an insulator 78 inserted therebetween. The first housing portion 80, which is spaced apart from a wrist 32, is grounded. The sensing device further includes a resistor 84 whose opposite ends are connected to the first and second housing portions 80, 82, respectively. The voltage between the opposite ends of the resistor 84 is changed when a high frequency current flows from the electric knife 72 to the second housing portion 82 of the detector probe 33. Thus, it is possible to detect use of the electric knife 72, by employing the sensing device of FIG. 8. The same reference numerals as used in the embodiment of FIG. 2 are used in FIG. 8 to designate the corresponding elements or parts of the modified embodiment.

Furthermore, while in the illustrated embodiment the pressure sensing diodes 60 are used as sensor means for detecting a pulse wave, it is possible to replace the diodes 60 with one or more other pressure sensing elements such as a pressure sensing transistor, a semiconductor strain gauge, or a non-semiconductor pressure sensing element.

Although a pulse wave is detected from the radial artery 54 in the illustrated embodiment, it is possible to detect a pulse wave from a dorsal pedal artery or a carotid artery, or a vein.

While the present invention has been described in a blood pressure monitoring apparatus, or a pulse wave detecting device therefor, the invention is applicable to other apparatus which are adapted to detect or utilize a heartbeat synchronous wave produced from a subject in synchronization with heartbeat of the subject; such as a pulse oxymeter, a photoelectric pulse wave detecting device, and an electrocardiograph.

It is to be understood that the present invention may be embodied with other modifications, changes, and improvements that may occur to those skilled in the art without departing from the scope and spirit of the invention defined in the appended claims.

What is claimed is:

1. An apparatus for detecting a heartbeat synchronous wave produced from a subject in synchronization with heartbeat of the subject, comprising:
    a probe which is adapted to be set on a body portion of said subject;
    first sensor means supported by said probe, for detecting said heartbeat synchronous wave from said body portion of said subject;
    second sensor means supported by said probe, for detecting a high frequency an electric current flowing from electric knife to said probe via said body portion;
    judging means for judging whether or not said electric knife is being used on said subject, based on the electric current detected by said second sensor means; and
    means for, if said judging means judges that said electric knife is being used, ceasing from detecting said heartbeat synchronous wave, or discarding the heartbeat synchronous wave detected when said electric knife is being used.

2. The apparatus as set forth in claim 1, wherein the detection of said electric current by said second sensor means is independent of the detection of said heartbeat synchronous wave by said first sensor means.

3. An apparatus for detecting a pulse wave produced from an arterial vessel of a subject in synchronization with heartbeat of the subject, comprising:
    a probe which is adapted to be set on a body portion of said subject;
    first sensor means supported by said probe, for detecting a pulse wave produced from an arterial vessel in said body portion of said subject;
    second sensor means supported by said probe, for detecting a high frequency electric current flowing from an electric knife to said probe via said body portion, the detection of said high frequency electric current being independent of the detection of said pulse wave; and
    judging means for judging whether or not said electric knife is being used on said subject, based on the detected high frequency electric current.

4. The apparatus as set forth in claim 3, further comprising means for ceasing, if said judging means judges that said electric knife is being used, from reading in said pulse wave detected by said first sensor means.

5. The apparatus as set forth in claim 3, further comprising
    means for discarding, if said judging means judges that said electric knife is being used, the heartbeat pulse wave detected when said electric knife is being used.

6. The apparatus as set forth in claim 3, wherein said sensor means comprises
    at least one pressure sensing element, and
    a temperature sensing resistor means for sensing a temperature of said at least one pressure sensing element, said resistor means producing an electric signal representative of a body temperature of said body portion of said subject,
    said second sensor means comprising said temperature sensing resistor means, a magnitude of said electric signal being changeable upon flowing of said high frequency electric current to said at least one pressure sensing element via said body portion of said subject, said second sensor means detecting said high frequency electric current based on the changed magnitude of said electric signal.

7. The apparatus as set forth in claim 3, wherein said probe comprises
    a housing including a first and a second portion each formed of an electrically conductive material, and an electrically insulating member inserted between said first and second portions, said first portion being grounded and spaced from said body portion of said subject while said second portion contacting said body portion,
    said second sensor means comprising said housing, and a resistor member connected at opposite ends thereof to said first and second portions of said housing, respectively, a voltage between the opposite ends of said resistor member being changeable upon flowing of said high frequency electric current to said second portion of said housing via said body portion of said subject, said second sensor means detecting said high frequency electric current based on the changed voltage between the opposite ends of said resistor member.

8. The apparatus as set forth in claim 3, wherein said judging means judges that said electric knife is being used, if said judging means detects a high frequency electric current greater than a first reference value.

9. The apparatus as set forth in claim 8, wherein said judging means judges that said electric knife is being used, if said judging means continues to detect said high frequency electric current for more than a first reference time.

10. The apparatus as set forth in claim 9, further comprising, when said judging means is a first judging means,
    a second judging means for judging whether or not said electric knife is not being used any longer after use thereof.

11. The apparatus as set forth in claim 10, wherein said second judging means judges that said electric knife is not being used any longer, if said second judging means detects that the high frequency electric current greater than said first reference value has become smaller than a second reference value smaller than said first reference value.

12. The apparatus as set forth in claim 11, wherein said second judging means judges that said electric knife is not being used any longer, if said second judging means continues to detect the high frequency electric current smaller than said second reference value for more than a second reference time.

13. The apparatus as set forth in claim 12, wherein said second judging means further judges whether or not said subject has become free from said high frequency electric current and highly stable after the use of said electric knife.

14. The apparatus as set forth in claim 3, further comprising
- means for storing the pulse wave detected by said first sensor means when said electric knife is not being used, and
- means for utilizing, if said judging means judges that said electric knife is being used, the pulse wave detected and stored before the use of said electric knife.

15. The apparatus as set forth in claim 3, further comprising means for determining a blood pressure of said subject based on the pulse wave detected by said first sensor means when the electric knife is not being used on said subject.

16. An apparatus for detecting a heartbeat synchronous wave produced from a subject in synchronization with heartbeat of the subject, comprising:
- a probe which is adapted to be set on a body portion of said subject;
- sensor means for detecting said heartbeat synchronous wave produced from said subject, said sensor means being supported by said probe;
- judging means for detecting a high frequency electric current flowing from an electric knife to said probe via said body portion, and judging whether or not said electric knife is being used on said subject, based on the detected high frequency electric current;
- said sensor means comprising at least one pressure sensing element, and a temperature sensing resistor means for sensing a temperature of said at least one pressure sensing element, said resistor means producing an electric signal representative of a body temperature of said body portion of said subject; and
- said judging means comprising said temperature sensing resistor means, a magnitude of said electric signal being changeable upon flowing of said high frequency electric current to said at least one pressure sensing element via said body portion of said subject, said judging means detecting said high frequency electric current based on the changed magnitude of said electric signal.

17. An apparatus for detecting a heartbeat synchronous wave produced from a subject in synchronization with heartbeat of the subject, comprising:
- a probe which is adapted to be set on a body portion of said subject;
- sensor means for detecting said heartbeat synchronous wave produced from said subject, said sensor means being supported by said probe;
- judging means for detecting a high frequency electric current flowing from an electric knife to said probe via said body portion, and judging whether or not said electric knife is being used on said subject, based on the detected high frequency electric current;
- said probe comprising a housing including a first and a second portion each formed of an electrically conductive material, and an electrically insulating member inserted between said first and second portions, said first portion being grounded and spaced from said body portion of said subject while said second portion contacts said body portion; and
- said judging means comprising said housing, and a resistor member connected at opposite ends thereof to said first and second portions of said housing, respectively, a voltage between the opposite ends of said resistor member being changeable upon flowing of said high frequency electric current to said second portion of said housing via said body portion of said subject, said judging means detecting said high frequency electric current based on the changed voltage between the opposite ends of said resistor member.

18. An apparatus for detecting a heartbeat synchronous wave produced from a subject in synchronization with heartbeat of the subject, comprising:
- a probe which is adapted to be set on a body portion of said subject;
- sensor means for detecting said heartbeat synchronous wave produced from said subject, said sensor means being supported by said probe;
- first judging means for detecting a high frequency electric current flowing from an electric knife to said probe via said body portion, and judging whether or not said electric knife is being used on said subject, based on the detected high frequency electric current;
- wherein said first judging means judges that said electric knife is being used, if said judging means detects a high frequency electric current greater than a first reference value for more than a first reference time; and
- second judging means for judging whether or not said electric knife is not being used any longer after use thereof, if said second judging means detects that the high frequency electric current greater than said first reference value has become smaller than a second reference value smaller than said first reference value.

19. The apparatus as set forth in claim 18, wherein said second judging means judges that said electric knife is not being use any longer, if said second judging means continues to detect the high frequency electric current smaller than said second reference value for more than a second reference time.

20. The apparatus as set forth in claim 19, wherein said second judging means further judges whether or not said subject has become from said high frequency electric current and is highly stable after the use of said electric knife.

* * * * *